United States Patent
Van Hille et al.

(10) Patent No.: US 6,810,756 B2
(45) Date of Patent: Nov. 2, 2004

(54) SAMPLING DEVICE

(75) Inventors: Carine Van Hille, Voisins le Bretonneux (FR); Dominique Roy, Domfront (FR); Pierre-Emmanuel Cognet, Versailles (FR)

(73) Assignee: Compagnie Generale Des Matieres Nucleaires, Velizy-Villacoublay (FR)

( * ) Notice: Subject to any disclaimer, the term of this patent is extended or adjusted under 35 U.S.C. 154(b) by 293 days.

(21) Appl. No.: 10/018,157

(22) PCT Filed: Apr. 4, 2001

(86) PCT No.: PCT/FR01/01010
§ 371 (c)(1),
(2), (4) Date: Dec. 6, 2001

(87) PCT Pub. No.: WO01/77642
PCT Pub. Date: Oct. 18, 2001

(65) Prior Publication Data
US 2002/0157468 A1 Oct. 31, 2002

(30) Foreign Application Priority Data
Apr. 6, 2000 (FR) .............................. 00 04387

(51) Int. Cl.⁷ .................................................. G01N 1/00
(52) U.S. Cl. .................................................. 73/863.73
(58) Field of Search ........................ 73/863.71–863.73, 73/863.81, 863.83–863.86, 864, 864.34, 864.35

(56) References Cited

U.S. PATENT DOCUMENTS

| 2,864,254 | A | | 12/1958 | McDonald | |
|---|---|---|---|---|---|
| 3,321,977 | A | * | 5/1967 | Topham | 73/863.71 |
| 4,085,618 | A | | 4/1978 | Collins | |
| 4,133,736 | A | * | 1/1979 | Nakagawa et al. | 73/864.34 |
| 5,905,213 | A | * | 5/1999 | Jaeger | 73/863.85 |
| 5,925,833 | A | | 7/1999 | Peterson | |

FOREIGN PATENT DOCUMENTS

| DE | 298 00 967 U1 | 4/1998 |
|---|---|---|
| NL | 1 008 931 | 10/1999 |

* cited by examiner

Primary Examiner—Robert Raevis
(74) Attorney, Agent, or Firm—Pearne & Gordon LLP

(57) ABSTRACT

A rotating plug (4) is installed in a body (1) and can be in different positions in which two lateral drillings come in front of the orifices corresponding to the body (1) or a sampling orifice (18) in front of which a flask is placed. The fluid to be sampled is circulated so that it fills a chamber (12) delimited by the rotating plug (4), and the rotating plug is then turned until one of its drillings is facing the sampling orifice (18) and a piston (11) delimiting the chamber (12) is pushed in to extract the required quantity of the sample. This device is simple and has an excellent seal.

9 Claims, 3 Drawing Sheets

SAMPLING DEVICE

Figure 1:
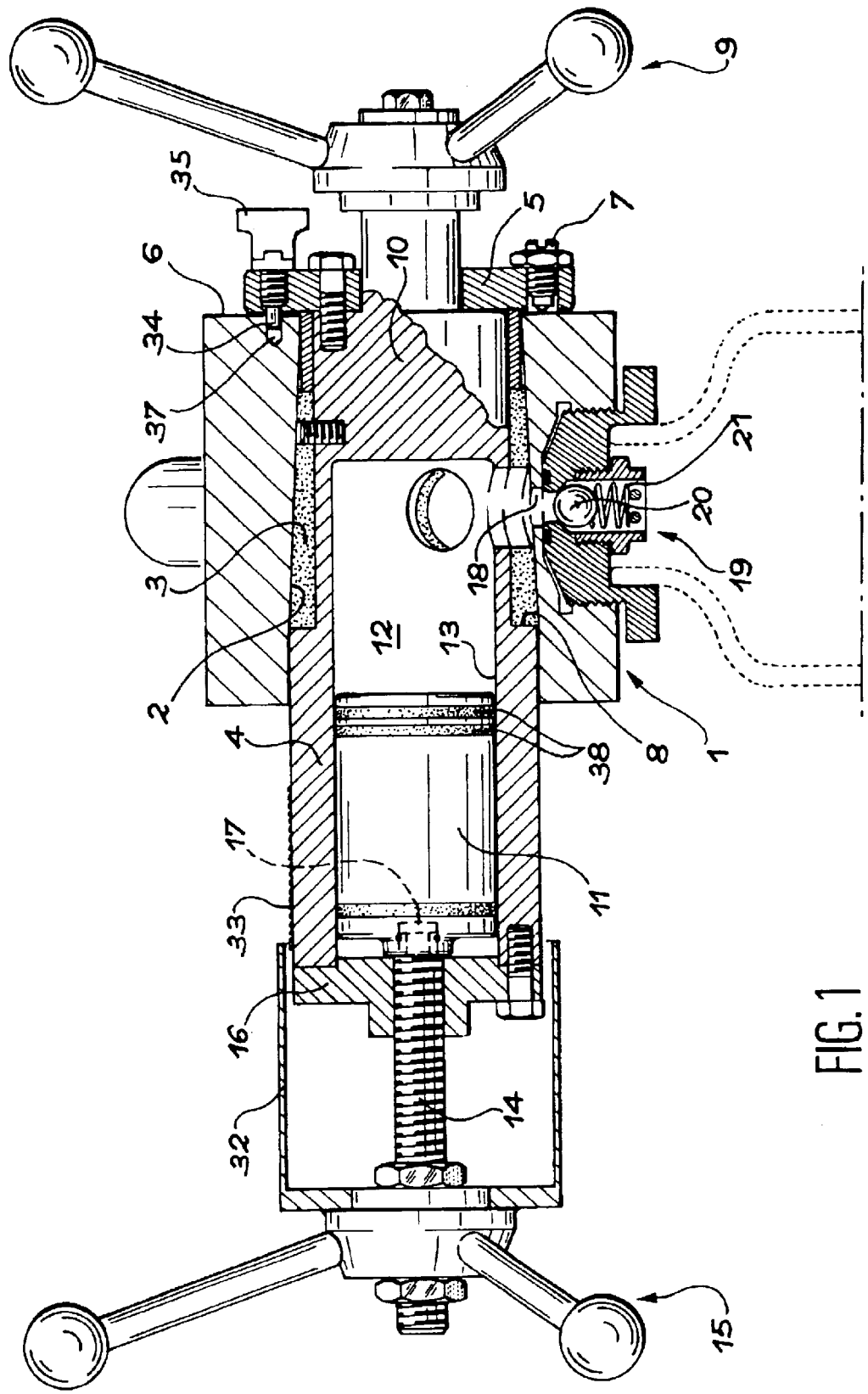

This document describes a device for taking samples, particularly pasty and muddy samples that can have very variable viscosity characteristics.

Some devices can be used to take fluid samples from a reservoir before they are forced out by the displacement of a piston that contributes to delimiting a chamber with variable volume into which the samples are drawn. One of these devices, known to everyone, is a syringe. Another device developed by the applicant for taking mud samples, is described in French patent booklet 2 700 851. It comprises a membrane formed by a circular elastic casing, that is inflated to close off the sampling chamber and is deflated to open it. The area of the opening may be equal to the cross-section of the chamber (cylindrical) if the casing continues along the line of the wall of the chamber when it is deflated, which means that very viscous samples can be drawn in easily without them being disturbed by flow irregularities. However, this device can only be used to take samples on site, whereas it is often more convenient and less dangerous, or advisable for other reasons, to take samples passing through a pipe.

With another type of fluid sample-taking device, an example of which is described in French patent 2 747 780, the product to be sampled is drawn in precisely through a pipe with two adjacent elbows interrupted in front of these elbows. The edge of the receptacle in which the sample is to be collected is placed around the elbows, such that the receptacle restores continuity of the pipe and the product drawn in passes through it. This device is particularly simple, and the regularity of the pipe cross-section is such that different viscosities of samples can be taken without very much changing their physical composition; But it is not possible to control the sampled volume, except by choosing a receptacle with the required volume, which is not very convenient and is sometimes impossible under real circumstances in laboratories; furthermore, receptacles are open, which means that they must be kept within a protection chamber if the samples are dangerous.

The essential purpose of the invention is to safely and simply take fluid samples that can have variable and possibly high values of viscosity and cloudiness. In particular, it is desirable not to have to dip the sampling device into the product, and to keep the sampled product within an entirely closed and sealed volume for the time necessary to transport it or to submit it to a first examination without being exposed to the product; the sample may be refused and rejected without having taken any risk.

The device comprises a body inside which there is a rotating plug through which two drillings have been made, separated by an angle equal to an angle separating two orifices penetrating the body and leading into an intake pipe and a discharge pipe for the unsampled part of the effluent, the body also being perforated by a sample-taking orifice provided with a calibrated valve located between the bottom of a cylindrical chamber contained in the body and partially delimited by the rotating plug, the device also comprising a piston free to move in the rotating plug towards and away from the bottom and delimiting the chamber on the side opposite the bottom.

Note that although some elements according to prior are present in the invention, they are combined in an innovative manner that can be considered to be unexpected; the use of a body and a rotating plug makes one think of a valve, but valves are only designed to enable and interrupt a flow without enabling collection of a sample of the flowing liquid in themselves; there is a piston that varies the volume of a chamber, but this piston does not draw the sample into the chamber; finally, the sample is formed by creating a flow that passes through a chamber for which the contents are to be sampled, but this chamber is not included in a removable flask as in earlier designs.

The seal of the device and its ease of maintenance are better if the bottom of the chamber is delimited by a base of the rotating plug, the sampling orifice is located on a circumference of the body common to the inlet and discharge orifices, and is separated from one of the inlet and outlet orifices by the angle between the drillings in the rotating plug.

In one particularly simple embodiment of the structure, an opening is formed in the body opposite the bottom of the chamber, the rotating plug projects from the body at the said opening, the piston is coupled to a manoeuvring device fitted with a portion engaged by a thread on the rotating plug; the sampled volume may be adjusted very easily if the said portion of the manoeuvring device is a skirt covering the rotating plug and if the graduations are marked on the rotating plug, to be covered by the skirt when the piston is displaced.

The invention will now be described by means of a specific embodiment, which is now the preferred embodiment and is shown in the following figures:

FIG. 1 is a cross-sectional view of the device, and the other FIGS. 2A, 2B, 2C and 2D are cross-sectional views that illustrate the possible positions of the rotating plug in the body.

A fixed part of the device proposed in this patent is a body 1 forming an approximately cylindrical hollow body and opened at both ends; however, its internal face is provided with a conical wall 2 that acts as a seat to a sealing ring 3 engaged around a rotating plug 4 screwed to it and provided with a complementary taper to provide a tight and sealed adjustment between the body 1 and the rotating plug 4. Since a shoulder 8 of the rotating plug 4 comes into contact with the end of the ring 3 pointing towards the opening of the conical surfaces, the edge of ring 3 is pressed into contact with the conical wall 2 by pushing the rotating plug 4 towards the top of the cone of the wall 2. The rotating plug 4 is kept in its longitudinal position in body 1 with sufficient thrust on ring 3 by a flange 5 screwed to rotating plug 4 and bearing on a plane face 6 of the body 1 oriented towards to said top of the cone that makes it impossible to extract the rotating plug 4. Stop screws 7 engaged through the flange 5 and for which the rounded head is in contact on face 6 can be used to modify the penetration of the rotating plug 4 in the body 1, for example if there is any wear in the sealing ring 3. The rotating plug 4 continues beyond the flange 5 in a handle 9 that is used to rotate it.

The rotating plug 4 is equipped with a base 10 adjacent to the flange 5 that closes it on this side while it is open at its opposite end, but a piston 11 closes off the opening and contributes to delimiting a cylindrical chamber 12 with the base 10 and the internal lateral face 13 of the rotating plug 4. The piston 11 depends on a threaded pin 14 manoeuvred by a handle 15 opposite the handle 9 and engaged by screwing into a flange 16 fixed to the rotating plug 4. The rotation of the handle 15 and the spindle 14 results in a sliding movement of the piston 11 that varies the volume of the chamber 12. Since the threaded spindle 14 ends at a button 17 engaged in the material of the piston 11 while being free to rotate in it, the piston 11 remains fixed in rotation.

The body 1 comprises three orifices, including a sampling orifice 18 that can clearly be seen in FIG. 1; it is closed by a valve 19 composed of a ball 20 calibrated by a spring 21 to enable the sampling orifice 18 to open when the pressure in the chamber 12 is high enough. A flask shown in dashed lines can be pressed around the sampling orifice 18 and the valve 19 to collect a sample that would be discharged from chamber 12.

Figure 2A:
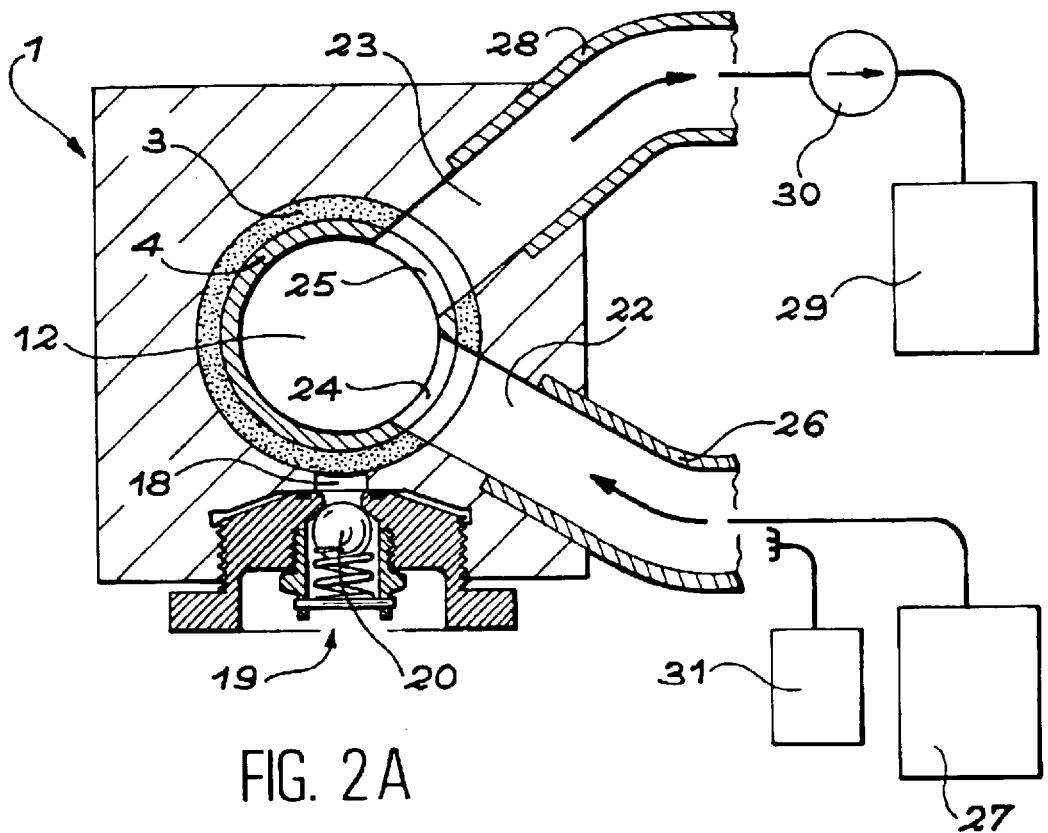

The other FIGS. 2A, 2B, 2C and 2D show the other two orifices that penetrate through body 1; an inlet orifice 22 of the sample and a fluid discharge orifice 23 that is not sampled. The orifices 18, 22 and 23 are arranged around the same circumference such that an equal angle separates orifices 18 and 22 and orifices 22 and 23. Furthermore, the rotating plug 4 and the ring 3 are penetrated by two drillings 24 and 25 located at the same height as the orifices 18, 22 and 23 and separated by the same angle. As the rotating plug 4 rotates in the body 1 and the drillings 24 and 25 pass in front of the orifices 18, 22 and 23, the device may be in one of four main states illustrated in FIGS. 2A and 2D. The state in FIG. 2A is a state in which the product to be sampled flows from an inlet conduit 26 terminating at the inlet orifice 22 and output from a reservoir 27 from which the product is drawn off, to a discharge pipe 28 adjacent to orifice 23 and leading to a discharge reservoir 29. A pump 30 formed between reservoirs 27 and 29, preferably on the discharge pipe 28 to avoid disturbing the physical composition of the sample on the input side of the device, sets up this flow through the device and the chamber 12, the drillings 24 and 25 of the rotating plug 4 coming in front of the orifices 22 and 23 respectively in the body; the sampling orifice 18 is then closed by rotating plug 4.

Figure 2B:
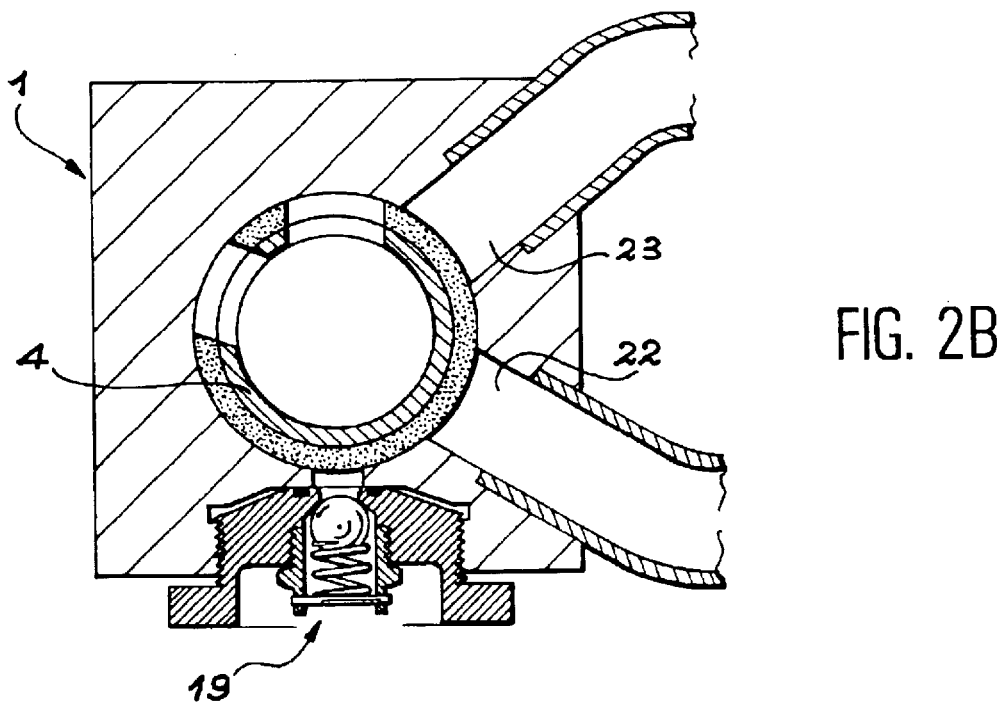
Figure 2C:
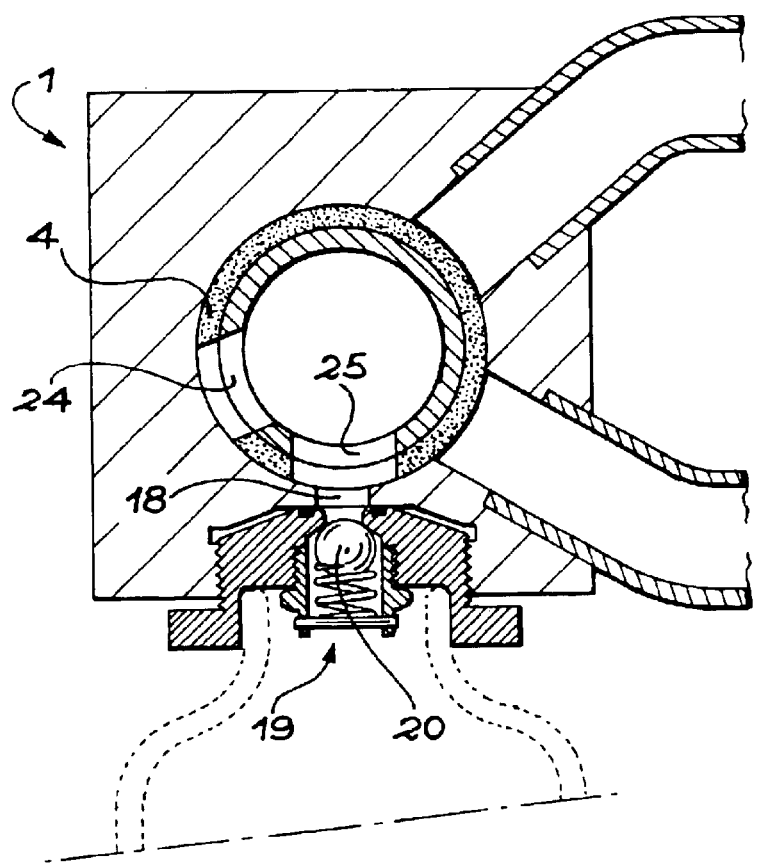

When the flow has been running for long enough for a representative sample of the fluid to enter the chamber 12, the rotating plug 4 may be rotated as far as the position in FIG. 2B, where the drillings 24 and 25 are facing the blind portions of the body 1 and in which the orifices 18, 22 and 23 in the body are all closed. The chamber 12 is then closed, and the time necessary to take measurements characteristic of the sample is available, particularly for making radiological measurements or measurements using the chosen sensors (not shown) fitted on the rotating plug 4 and leading into the chamber 12. The sample may be replaced if it is considered that it is not suitable, by replacing the rotating plug 4 in the position shown in FIG. 2A; otherwise, it may be decided to take a sample putting the rotating plug into the position in FIG. 2C, in which the drilling 25 of the rotating plug 4 is in front of the sampling orifice 18 and in which the other drilling 24 is still in front of a closed part of the body 1, the orifices 22 and 23 remaining closed.

It is then possible to discharge the piston 11 by rotating the handle 15 to reduce the volume of the chamber 12 and force a volume of the sample to pass out of the device through the sampling orifice 18, where it is collected by the flask mentioned above.

The end of a typical sampling manoeuvre consists of activating a pump 31 connected to the pipe 26 to inject water or another rinsing liquid in the inlet orifice 22, after bringing the rotating plug 4 into the position shown in FIG. 2A and after discharging the piston 11 at the position pushed furthest into the rotating plug 4: the sample remaining in the chamber 12 is discharged to the discharge reservoir 29 by piston 11, and then by the rinsing liquid which therefore washes orifices 22 and 23 and chamber 12.

Figure 2D:
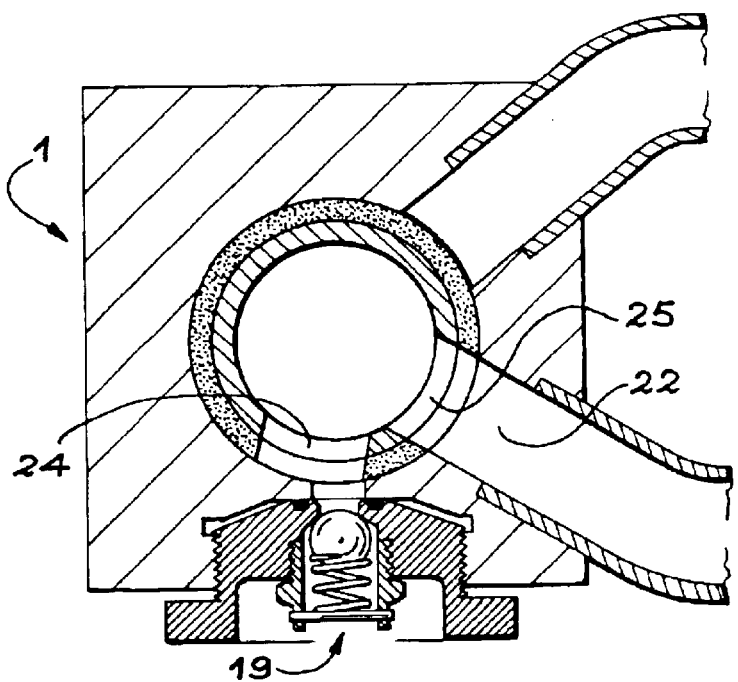

A final rotation of the rotating plug 4, bringing it to the position shown in FIG. 2D in which the drillings 24 and 25 are located in front of the sampling orifice 18 and the inlet orifice 22 respectively, to spray a rinsing liquid into the inlet orifice at a sufficiently high pressure to open the valve 19 and finish washing the device, the rinsing effluent being rejected through orifice 18. Another sample can then be taken. Since the device is then perfectly clean, it can also be manipulated without any risk.

Returning to FIG. 1, it can be seen that the handle 15 can be provided with a skirt 32 covering one end of the rotating plug 4 projecting from the body 1 and on which graduations 33 were drawn. When the piston 11 is pressed in, the skirt 32 covers these graduations 33 one after the other to quantify the variation of the chamber 12 and the sampled volume. This feature is very useful with dangerous samples, since in this case all that is sampled is an acceptable quantity defined by a threshold.

Rotation of the rotating plug 4 is facilitated if the flange S is provided with a sliding pin 34 that can be pulled by a button 35 but which returns to a penetration position under the action of a spring, in which it penetrates into the holes 37 formed in the body 1 and that define special positions (as shown in FIG. 2) of the rotating plug 4. Only one of these holes 37 can be seen in FIG. 1, but the other holes are identical.

The ring 3 made of a material with a low coefficient of friction and compressed between the body 1 and the rotating plug 4, creates a sufficiently good seal around drillings 24 and 25, the bottom 10 of the rotating plug 4 hermetically closes the chamber 12 on one side, and the piston 11 is provided with seals 38 that produce the same effect on the other side of the chamber 12. Therefore, at the very worst, sample leaks are very small.

Maintenance of the device is easy due to the simple shapes of its elements, and in particular it is easy to open body 1 at both ends; it can immediately be seen that the device can be completely disassembled very simply be removing a few screws, to perform all required maintenance and cleaning tasks.

Finally, it is just as easy to manoeuvre the device, since it only depends on two handles 9 and 5 at opposite ends of the device and in easily accessible areas.

What is claimed is:

1. Sample-taking device, comprising a body (1) inside which there is a rotating plug (4) through which two drillings (24, 25) have been made, separated by an angle equal to an angle separating two orifices (22, 23) penetrating the body (1) and which are an inlet orifice and an outlet orifice, and respectfully leading into a sample intake pipe and discharge pipe, the body also being perforated by a sample-taking orifice (18) provided with a check valve (19) located at the bottom of a cylindrical chamber (12) contained in the body and partially delimited by the rotating plug (4), the device also comprising a piston (11) free to move in the rotating plug (4) towards and away from the bottom and delimiting the chamber on the side opposite the bottom.

2. Sample-taking device according to claim 1, characterized in that the bottom of the chamber (12) is delimited by a base (10) of the rotating plug (4), the sampling orifice (18) is located on a circumference of the body common to the inlet and outlet orifices, and is separated from one of the inlet and outlet orifices (22, 23) by the angle between the drillings (24, 25) in the rotating plug.

3. Sample-taking device according to either of claim 1, characterized in that an opening is formed in the body (1) opposite the bottom of the chamber, the rotating plug (4) projects from the body at the said opening, and in that the piston is coupled to a manoeuvring device (15) fitted with a portion engaged by threading on the rotating plug.

4. Sample-taking device according to claim 3, characterized in that the said portion of the manoeuvring device is a skirt (32) covering the rotating plug (4) and in that the graduations (33) are marked on the rotating plug.

5. Sample-taking device according to claim 3, comprising a manoeuvring device (9) for the rotating plug opposite to the piston manoeuvring device (15).

6. Sample-taking device according to claim 1, characterised in that the rotating plug (4) is separated from the body (1) by a sealing ring (3).

7. Sample-taking device according to claim 6, characterised in that the sealing ring (3) and the body (1) bear on conical surfaces (2), in that the rotating plug (4) is connected to the body (1) through a system for adjusting the position of the rotating plug (4) along a rotation spindle of the rotating plug (4), and in that the sealing ring is in contact with the rotating plug, in the direction of the opening of the conical surfaces.

8. Sample-taking device according to claim 7, characterised in that the layout of the position setting of the rotating plug (4) is composed of a flange (5) formed on the rotating plug (4) and provided with adjustment screws (7) bearing on the body (1).

9. Sample-taking device according to claim 8, characterised in that the flange (5) is provided with a stop pin (34) preventing rotation of the rotating plug (4) and the body (1) is provided with holes (37) formed on a circular trajectory of the pin (34) when the rotating plug (4) is rotated, and that define the preferred stop positions for the rotating plug.

\* \* \* \* \*